United States Patent [19]

Sun

[11] 4,351,957
[45] Sep. 28, 1982

[54] PROCESS FOR PREPARING DIAMINODIPHENYL-ALKANES

[75] Inventor: Kwok K. Sun, Hamden, Conn.

[73] Assignee: The Upjohn Company, Kalamazoo, Mich.

[21] Appl. No.: 53,378

[22] Filed: Jun. 29, 1979

[51] Int. Cl.³ ............................................. C07C 87/50
[52] U.S. Cl. .................................. 564/331; 549/336; 549/344; 549/388; 549/406; 564/322; 564/333
[58] Field of Search ........................ 260/570 D, 345.5; 564/322, 331, 333

[56] References Cited

U.S. PATENT DOCUMENTS 3,418,371 12/1968 Krimm et al. ....................... 260/570
4,052,466 10/1977 Sun ............................... 260/345.5 X

FOREIGN PATENT DOCUMENTS 502860 3/1939 United Kingdom ................ 260/570

Primary Examiner—Robert V. Hines
Attorney, Agent, or Firm—Denis A. Firth; John Kekich

[57] ABSTRACT

A process is described for the preparation of bis-(aminophenyl)alkanes and bis(aminophenyl)cycloalkanes which comprises condensing a m-alkylphenol with an alkanone or cycloalkanone and heating the resulting condensation product with an at least stoichiometric amount of an acid addition salt of aniline or a substituted aniline or a mixture of such amines.

13 Claims, No Drawings

PROCESS FOR PREPARING DIAMINODIPHENYL-ALKANES

BACKGROUND OF THE INVENTION

1. Field of the Invention

This invention relates to a process for the preparation of substituted diphenylalkanes and is more particularly concerned with an improved synthesis of di(aminophenyl)alkanes.

2. Description of the Prior Art

Various methods are known for the preparation of 2,2-bis(4-aminophenyl)propane and like bis(aminophenyl)alkanes. Illustratively, the former has been prepared by the condensation of acetone and aniline hydrochloride; see U.S. Pat. No. 3,670,024. An earlier process for the same compound involved the reaction of acetone and aniline under pressure in the presence of hydrochloric acid to yield the diamine in question in low yield; see U.S. Pat. No. 2,794,822. 2,2-Bis(4-aminophenyl)propane has also been prepared by direct amination of bisphenol A (see U.S. Pat. No. 3,860,650) and, as a by-product in low yield, by the reaction of bisphenol A with aniline (see U.S. Pat. No. 3,418,371). The main product of the latter reaction is 2-(4-hydroxyphenyl)-2-(4-aminophenyl)propane.

I have now found that 2,2-bis(4-aminophenyl)propane and related compounds can be obtained in high yield by an improved process which will be described below.

In my copending application Ser. No. 898,646 filed Apr. 21, 1978 and now U.S. Pat. No. 4,177,211 there is described a process for the preparation of 2,2-bis(4'-aminophenyl)propane and related compounds by reacting the corresponding 2,2-bis-(2,4-dialkoxyphenyl)alkanes with an aniline acid addition salt at elevated temperature. The process of the present invention represents an alternative route to the production of 2,2-bis(4'-aminophenyl)propane and related compounds from readily available, inexpensive starting materials via intermediates which are clearly different from those employed in the aforesaid copending application.

SUMMARY OF THE INVENTION

This invention comprises a process for the preparation of a bis(aminophenyl)alkane having the formula:

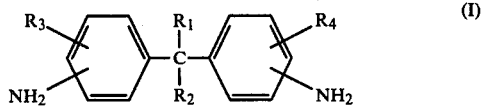

wherein $R_1$ and $R_2$, taken individually, each represent lower-alkyl, $R_1$ and $R_2$ taken together with the C atom to which they are attached represent the residue of a 1,1-cycloalkylidene group having from 5 to 7 ring carbon atoms, inclusive, and $R_3$ and $R_4$ are independently selected from the group consisting of hydrogen, lower-alkyl, lower-alkenyl and lower-alkoxy;

said process comprising the steps of (a) condensing a m-(lower-alkyl)phenol with a ketone selected from the class consisting of lower-alkanones of the formula $R_1COR_2$ and cycloalkanones containing from 5 to 7 ring carbon atoms in the proportion of at least 1 mole of m-lower-alkylphenol per mole of ketone and in the presence of an acid catalyst and;

(b) heating the resulting product at a temperature of 50° C. to 300° C. with at least 2 moles, per mole of said product, of an acid addition salt of at least one aromatic amine having the formula:

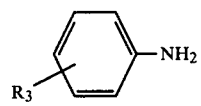

wherein $R_3$ has the meaning set forth above.

The term "lower-alkyl" means alkyl from 1 to 8 carbon atoms, inclusive, such as methyl, ethyl, propyl, butyl, pentyl, hexyl, heptyl, octyl and isomeric forms thereof. The term "lower-alkenyl" means alkenyl from 3 to 8 carbon atoms, inclusive, such as allyl, butenyl, pentenyl, hexenyl, heptenyl, octenyl and isomeric forms thereof. The term "lower-alkoxy" means alkoxy from 1 to 8 carbon atoms, inclusive, such as methoxy, ethoxy, propoxy, butoxy, pentyloxy, hexyloxy, heptyloxy, octyloxy and isomeric forms thereof. The term "1,1-cycloalkylidene having from b 5 to 7 ring carbon atoms, inclusive" means 1,1-cyclopentylidene, 1,1-cyclohexylidene, 1,1-cycloheptylidene, 2-methyl-1,1-cyclohexylidene, 2,2-dimethyl-1,1-cyclopentylidene, and the like alkyl-substituted 1,1-cycloalkylidenes.

Illustrative of the ketones $R_1COR_2$, wherein $R_1$ and $R_2$ are as above defined. are acetone, methyl ethyl ketone, methyl propyl ketone, di-ethyl ketone, dibutyl ketone, methyl hexyl ketone, methyl octyl ketone and the like.

The term "acid addition salt" means a salt with a mineral acid such as hydrochloric, hydrobromic, hydrofluoric, sulfuric and phosphoric acids, or with a strong organic acid such as alkyl and aryl sulfonic acids of which methanesulfonic, ethanesulfonic, benzenesulfonic and p-toluenesulfonic acids are examples, trichloro- and trifluoro-acetic acids and the like.

The bis(aminophenyl)alkanes of formula (I) which are produced in accordance with this invention are well-known compounds which are useful as curing agents for epoxy resins, as chain extenders in the preparation of polyurethanes and as monomers which can be converted by reaction with dicarboxylic acid halides to form polyamides and, by reaction with dicarboxylic acid anhydrides, to form polyimides using processes well-known in the art for the preparation of polyamides and polyimides from diamines. The bis(aminophenyl)alkanes of formula (I) can also be converted, by phosgenation using procedures conventional in the art, to the corresponding diisocyanates which can then be employed in the preparation of polyurethanes and like isocyanate-based polymers.

DETAILED DESCRIPTION OF THE INVENTION

The process of the invention is carried out in two steps. In the first step of the process the appropriate ketone $R_1COR_2$, wherein $R_1$ and $R_2$ have the significance above defined, is condensed with the appropriate m-(lower-alkyl)phenol under conditions well recognized in the art for the preparation of bisphenols such as Bisphenol A; see, for example, U.S. Pat. No. 4,052,466 for a summary of the art relating to this condensation.

Illustratively, the m-(lower-alkyl)phenol and the ketone are brought together in the presence of an acidic catalyst at a temperature which is generally within the range of about 0° C. to about 100° C. Although higher and lower temperatures can be employed in particular instances, the reaction temperature employed in a given situation is dependent generally on the nature of the acid catalyst.

The phenol and the ketone are employed in at least stoichiometric proportions, i.e. at least one mole of the phenol per mole of the ketone. Advantageously, the phenol is employed in amounts in excess of the above proportion and up to about 20 moles of the phenol per mole of the ketone. Preferably, the molar proportion of the phenol to the ketone is within the range of about 2:1 to about 8:1.

The acidic catalyst employed in the condensation can be any of a wide variety of materials such as mineral acids as exemplified by hydrochloric acid (anhydrous gas or concentrated acid), perchloric acid, sulfuric acid, phosphoric acid and the like; Lewis acids such as boron trifluoride (generally employed as the etherate to facilitate handling), zeolites, ion-exchange resins such as polystyrene polysulfonic acids, acid clays and the like. These catalysts can be employed alone or in combination with cocatalysts such as thioglycolic acid and phenolic ethers such as those disclosed in the aforesaid U.S. Pat. No. 4,052,466.

The acidic catalysts, either alone or in combination with the cocatalysts, are generally employed in amounts within the range of about 1 part to about 50 parts by weight per 100 parts by weight of the m-(lower-alkyl)phenol employed in the condensation.

The progress of the condensation can be followed using routine analytical procedures such as infrared spectroscopy, nuclear magnetic resonance spectroscopy, and the like, carried out on aliquots of the reaction mixture. When the reaction is adjudged to have reached the end-point, as determined by one or more of the above procedures, the desired product is isolated from the reaction mixture by routine procedures. Illustratively, the acid in the reaction mixture is neutralized with a base, such as sodium hydroxide, sodium carbonate, potassium hydroxide and the like and the neutralized mixture is extracted with an organic solvent from which extract the desired product is isolated by evaporation of the solvent. The product so obtained can be purified, if desired, by distillation or other conventional procedures to remove excess m-(lower-alkyl)phenol starting material before being employed in the second stage of the process of the invention.

It is found that, where the starting ketone is an alkanone, the product so obtained from the condensation of the m-(lower-alkyl)phenol and the ketone is generally a mixture of at least two products. The minor component of the mixture is a bisphenol of the formula

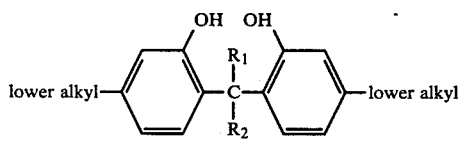 (III)

The major component of the mixture is a chroman derivative having the formula:

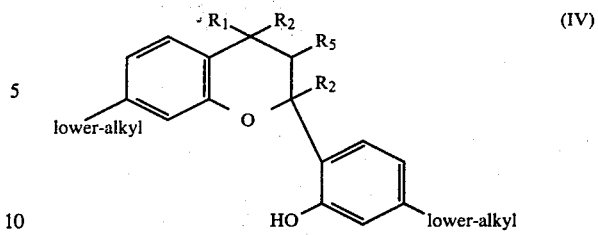 (IV)

wherein $R_1$ and $R_2$ have the significance hereinbefore defined, and $R_5$ is hydrogen or lower-alkyl. In the case of the condensation of the m-(lower-alkyl)phenol and a cycloalkanone the product is generally a mixture, the major components of which are the bisphenol of the above formula (III) and a chroman of the formula:

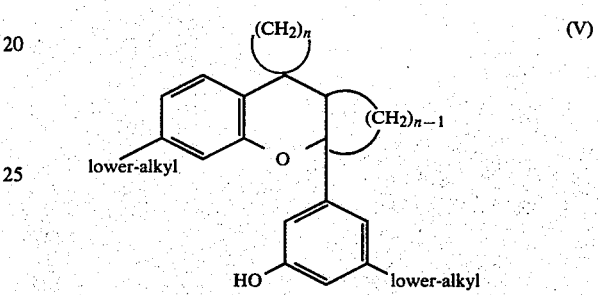 (V)

wherein n is an integer from 4 to 6.

Illustrative of the m-(lower-alkyl)phenols which can be employed in the above reaction are m-cresol, m-ethylphenol, m-propylphenol, m-butylphenol, m-hexylphenol, m-octylphenol and the like.

In the second step of the process of the invention the product obtained by condensation of the m-(lower-alkyl)phenol and the ketone in the first step of the process is heated at a temperature in the range of about 50° C. to about 300° C., preferably in the range of about 170° C. to about 250° C., with an acid addition salt of an aromatic amine of the formula (II) above or a mixture of two or more such aromatic amines. The acid addition salt is employed in a proportion which is at least 2 moles per mole of the reaction product from the first stage and preferably in the range of about 4 moles to about 20 moles per mole of said first stage reaction product.

The process of this second step of the invention can be represented schematically as follows:

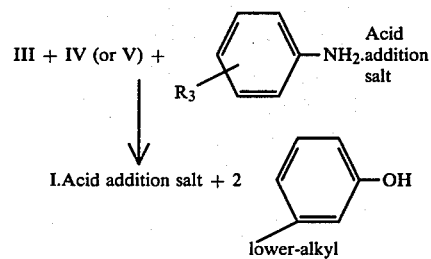

The progress of the reaction can be followed using conventional procedures, for example, by subjecting aliquots to infrared or nuclear magnetic resonance spectroscopy, or high pressure liquid chromatography. When the reaction is deemed complete, the resulting mixture of the desired bis(aminophenyl)alkane (I), in the form of its acid addition salt, and the recovered m-(lower-alkyl)phenol is separated by conventional procedures. For example, the mixture is subjected to extraction with organic solvents or to distillation under reduced pressure to remove the recovered phenol and the diamine salt which remains is purified by recrystallization, chromatography and like means, before or after being converted to the free diamine by neutralization with aqueous alkali metal hydroxide or carbonate. Alternatively, the above reaction mixture can be worked up by extracting the diamine salt in water, neutralizing the aqueous extract, and recovering the free diamine by solvent extraction.

The above reaction between the reaction product from the first step of the process of the invention and the acid addition salt of the aromatic amine (II) can be carried out equally satisfactorily in the presence or absence of an inert solvent. When no solvent is employed, the two reactants are intimately mixed and heated to the appropriate reaction temperature advantageously with agitation of the mixture using appropriate means. Optionally, the heating step can be carried out under reduced pressure whereby part, or the whole, of the m-(lower-alkyl)phenol liberated in the reaction distills out of the reaction mixture and thereby facilitates the subsequent recovery of the desired bis(aminophenyl)alkane from the reaction mixture.

Alternatively, the process of the invention can be carried out in the presence of an inert organic solvent, i.e. an organic solvent which does not enter into reaction with any of the initial reactants or the reaction products, or interfere in any other way with the desired course of the reaction. Illustrative of inert organic solvents are dichlorobenzene, trichlorobenzene, tetralin, decalin, trichlorophenol, and the like. Advantageously, when an inert organic solvent is employed, the acid addition salt of the aromatic amine (II) is dispersed or dissolved in the inert organic solvent and the mixture is heated with appropriate agitation to the desired reaction temperature before adding thereto a solution of the first stage reaction product in the inert organic solvent. The reaction is then carried out in the same manner and under the same conditions as described above for reaction in the absence of a solvent. The desired bis-(aminophenyl)alkane (I) is recovered by extracting the reaction mixture with water and neutralizing the aqueous extract with a base.

The m-(lower-alkyl)phenol which is recovered from the reaction product of the second stage of the process of the invention is obtained in substantially quantitative yield and can be re-used as the starting material in a subsequent run of the invention.

In an alternative embodiment of the process of the invention the reaction product from the first stage of the process is separated into its component parts, namely the bisphenol (III) and the chroman (IV) or (V), by routine procedures such as fractional crystallization, fractional distillation, chromatography and the like, and the individual components are subjected separately to the reaction with the acid addition salt of the aromatic amine (II). The reaction conditions employed are exactly the same as those described above for the reaction of the unseparated mixture of products from the first stage of the process.

Illustrative of the aromatic amines (II) employed in the process of the invention are aniline, o-toluidine, m-toluidine, o-ethylaniline, m-butylaniline, o-hexylaniline, o-octylaniline, o-methoxyaniline, o-butoxyaniline, m-octyloxyaniline and the like.

The following examples describe the manner and process of making and using the invention and set forth the best mode contemplated by the inventor of carrying out the invention but are not to be construed as limiting.

EXAMPLE 1

1. A mixture of 540 g. (5 mole) of redistilled m-cresol and 29.0 g. (0.5 mole) of acetone was stirred and maintained at 10°–20° C. while a slow stream of gaseous hydrogen chloride was bubbled in beneath the surface of the mixture over a period of 1.5 hour. The resulting mixture was then stirred for a further 3.5 hr. at ambient temperature (20°–25° C.). At the end of this period the mixture was diluted with 400 ml. of ether and the solution so obtained was washed successively with water, 5% w/v aqueous sodium carbonate solution and water. The washed solution was dried over anhydrous magnesium sulfate and the solvent was removed from the dried solution by evaporation. The residue was then subjected to distillation under reduced pressure (0.5 mm. of mercury, bath temperature 130° C.) to recover a total of 452.6 g. of m-cresol. The undistilled residue (74 g.) was distilled under reduced pressure to yield two fractions. The forecut (3.45 g.) had a boiling point of 150°–170° C. at 0.05 mm. of mercury and the bulk of the distillate A (70 g.) had a boiling point of 170°–180° C. at 0.05 mm. of mercury. Total yield of the condensation products based on acetone was 94.8% by weight. An aliquot (2.5 g.) of the main fraction was subjected to chromatography using a silica gel column (12"×1") which was eluted using petroleum ether followed by a mixture of petroleum ether and toluene (initially 2%; gradually increasing to 15% v/v). The first fraction was a trace amount of solid which was identified by nmr (nuclear magnetic resonance spectrum) as spiro[bis(4,4,7-trimethylchroman-2)] having the formula:

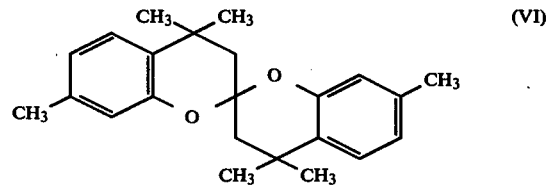

(VI)

The second and main fraction (94 molar percent of the mixture) was shown by nmr to be 2,4,4,7-tetramethyl-2-(2'-hydroxy-4'-methylphenyl)chroman corresponding to the formula:

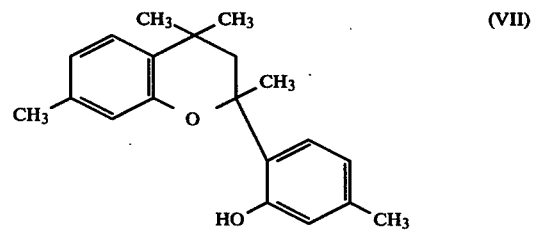

(VII)

The third fraction (5.9 molar percent of the mixture) was shown by nmr to be 2,2-bis(2'-hydroxy-4'-methylphenyl)propane corresponding to the formula:

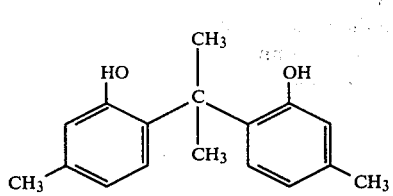

(VIII)

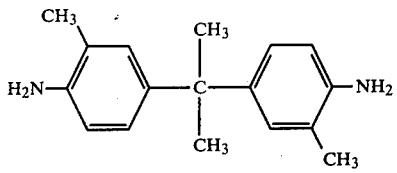

(IX)

2. A mixture of 2.69 g. (9.17 mmol. VII and 1.16 mmol. VIII) of distillate A (prepared as described in Part 1 above) and 20.8 g. (160 mmol.) of aniline hydrochloride was heated at 200° to 210° C. under nitrogen. After the aniline salt had melted, the mixture was stirred rapidly for 25 minutes at 205° to 215° C. before being cooled rapidly to room temperature. The cooled mixture was treated with a mixture of water and 10 ml. of 2 N hydrochloric acid and then extracted with chloroform. The aqueous phase was separated and extracted with chloroform and then with ether. The combined organic extracts were evaporated to give 2.87 g. of material which was distilled (100° C. and 0.05 mm. of mercury) to yield 1.94 g. of recovered m-cresol and 0.7 mmol. of incompletely converted VII. The aqueous phase from the above extractions was neutralized with 10 N aqueous sodium hydroxide and then extracted with two portions of chloroform. The chloroform extracts were combined and dried over anhydrous sodium sulfate before removing the chloroform by distillation. The residue (16.14 g.) was distilled under reduced pressure to give 11.3 g. of recovered aniline and 3.82 g. of 2,2-bis-(4'-aminophenyl)propane having a purity of over 98% and representing a 91.3% yield based on converted VII and VIII.

EXAMPLE 2

A mixture of 4.41 g. (15 mmol.) of 2,4,4,7-tetramethyl-2-(2'-hydroxy-4'-methylphenyl)chroman (VII) (prepared as described in Example 1, Part 1) and 34.6 g. (240 mmol.) of o-toluidine hydrochloride was heated until molten (210° C.) and then stirred at 207°–226° C. for 20 minutes before being cooled. The cooled mixture was dissolved in water and extracted with chloroform. The aqueous phase was separated and again extracted with chloroform. The combined chloroform extracts were dried over anhydrous sodium sulfate and evaporated to remove the solvent. The residue (4.47 g.) was distilled to yield 3.77 g. of m-cresol. The aqueous layer remaining after the above extractions was made slightly alkaline by the addition of 10 N aqueous sodium hydroxide and then extracted with two portions of chloroform. The chloroform extracts were combined and dried over anhydrous sodium sulfate, the chloroform was evaporated and the residue was distilled under reduced pressure. There was thus obtained 18.33 g. of o-toluidine followed by a fraction consisting of a viscous oil which distilled at 180°–195° C. at 0.1 mm. of mercury. This fraction was redistilled at 198°–201° C. at 0.12 mm. of mercury to give, as a pale yellow oil, 6.51 g. (85.4 percent yield) of 2,2-bis-(3'-methyl-4'-aminophenyl)propane having the formula:

Analysis: Calcd. for $C_{17}H_{22}N_2$: C, 80.26; H, 8.72; N, 10.01. Found: C, 79.93; H, 8.87; N, 10.50.

EXAMPLE 3

A mixture of 4.56 g. (15 mmol.) of the distillate A of Example 1, Part 1 (a mixture of 94% VII and 5.9% VIII), 17.3 g. (120 mmol.) of o-toluidine hydrochloride and 15.6 g. (120 mmol.) of aniline hydrochloride was heated until molten (180° C.) and then heated and stirred at 210°±2° C. for 18 minutes before being cooled rapidly to room temperature. The cooled mixture was dissolved in water and extracted with chloroform. The aqueous phase was separated and again extracted with chloroform. The combined chloroform extracts were dried over anhydrous sodium sulfate and evaporated to remove the solvent. The residue (3.15 g.) was distilled under reduced pressure to yield 2.45 g. of m-cresol. The aqueous layer remaining after the above extractions was made slightly alkaline by the addition of 10 N sodium hydroxide and then extracted with two portions of chloroform. The chloroform extracts were combined and dried over anhydrous sodium sulfate, the chloroform was evaporated and the residue was distilled under reduced pressure. There was thus obtained 18.19 g. of a mixture of o-toluidine and aniline. The residue (5.83 g.) was shown by high pressure liquid chromatography to be a mixture of 2,2-bis(3'-methyl-4'-aminophenyl)propane (IX), 2-(4'-aminophenyl)-2-(3'-methyl-4'-aminophenyl)propane having the formula:

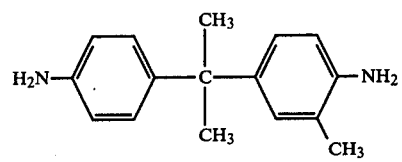

(X)

and 2,2-bis(4'-aminophenyl)propane in the molar proportions of 60:122.5:59.5. This mixture was distilled at 180°–205° C./0.1 mm. mercury. The three components in the mixture were separated by column chromatography using the same column and solvents as described in Example 1. Analysis for Compound (X): Calcd. for $C_{16}H_{20}N_2$: C, 79.95; H, 8.39, N, 11.66 Found: C, 80.20; H, 8.37; N, 11.60.

EXAMPLE 4

A mixture of 9.8 g. (100 mmol.) of cyclohexanone and 43.2 g. (400 mmol.) of m-cresol was stirred and maintained at 30°–40° C. while a slow stream of gaseous hydrogen chloride was bubbled in beneath the surface of the mixture over a period of 2 hours. After the introduction of hydrogen chloride had been completed, the mixture was stirred at room temperature for 16 hours before being diluted with ether. The ethereal solution was washed twice with water then with 5% aqueous sodium carbonate solution and finally with water. The washed solution was dried over anhydrous magnesium sulfate and the solvent was evaporated. The residue was distilled up to 100° C. at 0.2 mm. of mercury to recover 31.5 g. of m-cresol. The residue was 17.9 g. of a mixture of condensation products. A portion of this residue (7.52 g.) was mixed with 41.6 g. (320 mmol.) of aniline hydrochloride and the mixture was heated at 210°±5° C. for 20 minutes with stirring. The resulting mixture was cooled, dissolved in water, and extracted with methylene chloride. The aqueous phase was separated and made alkaline with 5 N sodium hydroxide solution before being extracted with three portions of a mixture of methylene chloride and ether. The combined solvent extracts were dried over anhydrous sodium sulfate and the solvent was evaporated. The residue (37.1 g.) was distilled up to 120° C. at 0.1 mm. of mercury to give 24.0 g. of aniline. The undistilled residue (5.95 g.) solidified slowly to yield crude 1,1-di(4'-aminophenyl)cyclohexane (56% yield). This material was purified by conversion to its dihydrochloride which was recrystallized from a mixture of methanol and acetone to give crystals of melting point 248°–249° C. The free diamine was regenerated (crystals melting point 112°–113° C.) from the dihydrochloride by neutralization of an aqueous solution of the latter with sodium hydroxide solution.

EXAMPLE 5

A mixture of 7.68 g. (30 mmol.) of 2,2-di(2'-hydroxy-4'-methylphenyl)propane (VIII) [prepared as described in Example 1, part 1] and 31.2 g. (240 mmol.) of aniline hydrochloride was heated at 200° to 210° C. with stirring for 20 minutes before being cooled rapidly. The resulting product was dissolved in water and extracted with two portions of methylene chloride followed by one portion of ether. The combined organic extracts were dried over anhydrous sodium sulfate and the solvent was evaporated. The residue (7.86 g.) was distilled to recover 5.7 g. of m-cresol and 3 mmol. of incompletely converted VIII. The aqueous phase, remaining after the above extractions, was made slightly alkaline by the addition of 10 N aqueous sodium hydroxide and then extracted with two portions of chloroform followed by two portions of ether. The combined organic extracts were dried over anhydrous sodium sulfate and evaporated to remove solvent. The residual brown oil (26.5 g.) was distilled to recover 16.7 g. of aniline and leave a residue (5.26 g.) of 2,2-bis(4'-aminophenyl)propane which was shown by high pressure liquid chromatography to have a purity of 98.9 percent representing a yield of 86 percent based on converted 2,2-di(2'-hydroxy-4'-methylphenyl)propane (VIII).

I claim:

1. A process for the preparation of a bis(aminophenyl)alkane having the formula:

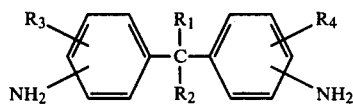

wherein $R_1$ and $R_2$, taken individually, each represent lower-alkyl, $R_1$ and $R_2$ taken together with the C atom to which they are attached represent the residue of a 1,1-cycloalkylidene group having from 5 to 7 ring carbon atoms, inclusive, and $R_3$ and $R_4$ are independently selected from the group consisting of hydrogen, lower-alkyl, lower-alkenyl and lower-alkoxy;

which process comprises the steps of (a) reacting a m-lower-alkylphenol with a ketone selected from the class consisting of lower-alkanones and cycloalkanones containing from 5 to 7 ring carbon atoms in the proportion of at least 1 mole of m-lower-alkylphenol per mole of ketone and in the presence of an acid catalyst and (b) heating the resulting product at a temperature of 50° C. to 300° C. with at least 2 moles, per mole of said product, of an acid addition salt of at least one aromatic amine having the formula:

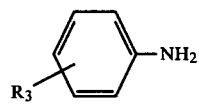

wherein $R_3$ has the meaning set forth above.

2. A process according to claim 1 wherein m-cresol is condensed with acetone in the presence of an acid catalyst, the molar proportion of m-cresol to acetone being at least 1:1, and the resulting product is heated at a temperature in the range of 50° C. to 300° C. with at least 2 moles, per mole of said product, of an aniline acid addition salt whereby there is obtained the acid addition salt of 2,2-bis(4'-aminophenyl)methane.

3. A process according to claim 1 wherein m-cresol is condensed with acetone in the presence of an acid catalyst, the molar proportion of m-cresol to acetone being at least 1:1, and the resulting product is heated at a temperature in the range of 50° C. to 300° C. with at least 2 moles, per mole of said product, of an acid addition salt of o-toluidine whereby there is obtained the acid addition salt of 2,2-bis(3'-methyl-4'-aminophenyl)propane.

4. A process according to claim 1 wherein m-cresol is condensed with acetone in the presence of an acid catalyst, the molar proportion of m-cresol to acetone being at least 1:1, and the resulting product is heated at a temperature in the range of 50° C. to 300° C. with at least 2 moles, per mole of said product, of a mixture of the acid addition salts of aniline and o-toluidine, whereby there is obtained a mixture of the corresponding acid addition salts of 2,2-bis(4'-aminophenyl)propane, 2,2-bis(3'-methyl-4'-aminophenyl)propane and 2-(4'-aminophenyl)-2-(3'-methyl-4'-aminophenyl)propane.

5. A process according to claim 1 wherein m-cresol is condensed with cyclohexanone in the presence of an acid catalyst, the molar proportion of m-cresol to cyclohexanone being at least 1:1, and the resulting product is heated at a temperature in the range of 50° C. to 300° C. with at least 2 moles, per mole of said product, of an acid addition salt of aniline whereby there is obtained the corresponding acid addition salt of 1,1-di(4'-aminophenyl)cyclohexane.

6. A process for the preparation of 2,2-bis(4'-aminophenyl)propane which comprises the steps of (a) condensing m-cresol with acetone in the presence of hydrogen chloride catalyst, the m-cresol being employed in an amount corresponding to at least 1 mole per mole of acetone; and (b) heating the resulting product at a temperature in the range of about 50° C. to 300° C. with an acid addition salt of aniline in a proportion of at least 2 moles of acid addition salt per mole of said compound to obtain 2,2-bis(4'-aminophenyl)propane in the form of an acid addition salt.

7. The process of claim 6 wherein the aniline acid addition salt is aniline hydrochloride and the 2,2-bis-(4'-aminophenyl)propane is obtained in the form of its dihydrochloride.

8. A process which comprises heating a mixture of 2,4,4,7-tetramethyl-2-(2'-hydroxy-4'-methylphenyl)-chroman and at least a stoichiometric proportion of an acid addition salt of at least one aromatic amine having the formula:

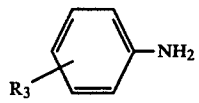

wherein R₃ is selected from the group consisting of hydrogen, lower-alkyl, lower-alkenyl and lower-alkoxy, at a temperature of 50° C. to 300° C. whereby there is obtained the corresponding acid addition salt of a bis(aminophenyl)propane of the formula:

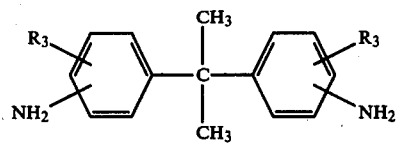

wherein R₃ has the significance above defined.

9. A process according to claim 8 wherein the aromatic amine is aniline and the resulting product is an acid addition salt of 2,2-bis(4'-aminophenyl)propane.

10. A process according to claim 8 wherein the aromatic amine is o-toluidine and the resulting product is an acid addition salt of 2,2-bis(3'-methyl-4'-aminophenyl)propane.

11. A process according to claim 8 wherein the aromatic amine is a mixture of aniline and o-toluidine and the resulting product is a mixture of the acid addition salts of 2,2-bis(4'-aminophenyl)propane, 2,2bis(3'-methyl-4'-aminophenyl)propane and 2-(4'-aminophenyl)-2-(3'-methyl-4'-aminophenyl)propane.

12. A process which comprises heating a mixture of 2,2-bis(2'-hydroxy-4'-methylphenyl)propane and at least a stoichiometric proportion of an acid addition salt of at least one aromatic amine having the formula:

wherein R₃ is selected from the group consisting of hydrogen, lower-alkyl, lower-alkenyl and lower-alkoxy, at a temperature of 50° C. to 300° C. whereby there is obtained the corresponding acid addition salt of a bis(aminophenyl)propane of the formula:

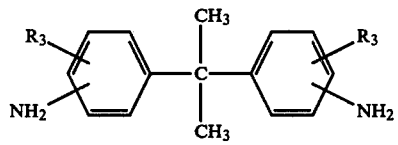

wherein R₃ has the significance above defined.

13. A process according to claim 12 wherein the aromatic amine is aniline and the resulting product is an acid addition salt of 2,2-bis(4'-aminophenyl)propane.

* * * * *

UNITED STATES PATENT OFFICE
CERTIFICATE OF CORRECTION

Patent No. 4,351,957      Dated September 28, 1982

Inventor(s) Kwok K. Sun

It is certified that error appears in the above-identified patent and that said Letters Patent are hereby corrected as shown below:

Column 2, line 21 "from b 5" should read --from 5--. Column 3, lines 60 to 65, that portion of the formula reading

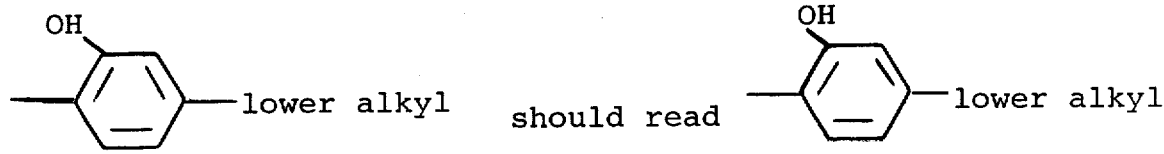

Column 7, lines 1 to 9, that portion of the formula reading

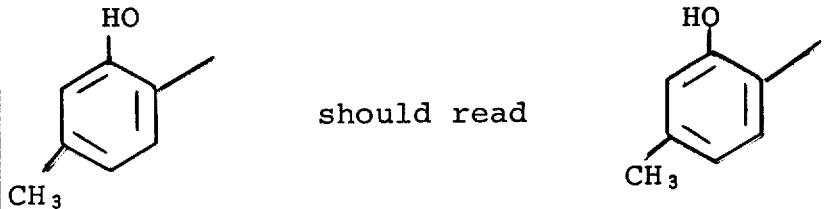

Signed and Sealed this

First Day of March 1983

[SEAL]

Attest:

GERALD J. MOSSINGHOFF

Attesting Officer      Commissioner of Patents and Trademarks